United States Patent
Fisk et al.

(10) Patent No.: US 10,407,391 B2
(45) Date of Patent: Sep. 10, 2019

(54) METHOD OF PREPARING BENZYL 4-AMINO-3-CHLORO-5-FLUORO-6-(4-CHLORO-2-FLUORO-3-METHOXY-PHENYL)PICOLINATE

(71) Applicant: Dow AgroSciences LLC, Indianapolis, IN (US)

(72) Inventors: Jason S. Fisk, Freeland, MI (US); David J. Couling, Midland, MI (US); Abraham D. Schuitman, Midland, MI (US); Megan E. Donaldson, Linwood, MI (US); Brian Murdoch, Midland, MI (US); Ronald B. Leng, Midland, MI (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 15/833,111

(22) Filed: Dec. 6, 2017

(65) Prior Publication Data

US 2018/0162814 A1    Jun. 14, 2018

Related U.S. Application Data

(60) Provisional application No. 62/433,415, filed on Dec. 13, 2016.

(51) Int. Cl.
| | | |
|---|---|---|
| *B01D 9/00* | (2006.01) | |
| *C07B 39/00* | (2006.01) | |
| *C07B 43/04* | (2006.01) | |
| *C07D 213/61* | (2006.01) | |
| *C07D 213/72* | (2006.01) | |
| *C07D 213/127* | (2006.01) | |
| *C07D 213/803* | (2006.01) | |

(52) U.S. Cl.
CPC .......... *C07D 213/127* (2013.01); *B01D 9/00* (2013.01); *B01D 9/005* (2013.01); *C07B 39/00* (2013.01); *C07B 43/04* (2013.01); *C07D 213/61* (2013.01); *C07D 213/72* (2013.01); *C07D 213/803* (2013.01)

(58) Field of Classification Search
CPC ..... C07B 39/00; C07B 43/04; C07D 213/127; C07D 213/61; C07D 213/72; C07D 213/803; B01D 9/00; B01D 9/005; F01C 1/00; F01K 23/08; F01K 27/02; F04C 18/0215; F04C 18/16; F04C 2210/26; F04C 29/026; F04C 29/04; F04D 17/10; F04D 29/063; F04D 29/5826; F04D 29/701; F25B 11/02; F25B 2400/141; F25B 2400/23; F25B 31/004; F25B 5/02
See application file for complete search history.

(56) References Cited

U.S. PATENT DOCUMENTS

| | | | |
|---|---|---|---|
| 3,742,060 A * | 6/1973 | Lagally | C07C 209/08 564/481 |
| 2007/0185346 A1* | 8/2007 | Vaidya | C07B 57/00 562/401 |
| 2014/0039196 A1* | 2/2014 | Whiteker | C07D 213/79 546/310 |

FOREIGN PATENT DOCUMENTS

WO    WO 2006/020664    *    2/2006

OTHER PUBLICATIONS

Matheson (Chem Eng News, 1960, 38, 30, p. 47). (Year: 1960).*

* cited by examiner

*Primary Examiner* — Umamaheswari Ramachandran

(57) ABSTRACT

A method of preparing benzyl 4-amino-3-chloro-5-fluoro-6-(4-chloro-2-fluoro-3-methoxyphenyl)picolinate (I) from benzyl 4,5-difluoro-6-(4-chloro-2-fluoro-3-methoxyphenyl)picolinate (II) is described. The method includes the use of amination and chlorination process steps to provide the compound of Formula I.

18 Claims, No Drawings

METHOD OF PREPARING BENZYL 4-AMINO-3-CHLORO-5-FLUORO-6-(4-CHLORO-2-FLUORO-3-METHOXYPHENYL)PICOLINATE

CROSS-REFERENCED TO RELATED APPLICATION

This application claims priority to U.S. Provisional Patent Application Ser. No. 62/433,415, filed Dec. 12, 2016, the disclosure of which is hereby incorporated herein in its entirety by this reference.

BACKGROUND

The current methods for preparing florpyrauxifen-benzyl (benzyl 4-amino-3-chloro-5-fluoro-6-(4-chloro-2-fluoro-3-methoxyphenyl)picolinate; I) are described in U.S. Pat. Nos. 8,609,855 and 8,871,943.

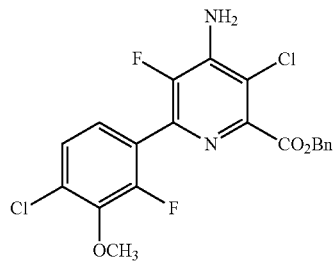

SUMMARY

A method for preparing florpyrauxifen-benzyl (i.e., the compound of Formula I) is provided. Specifically, the method involves converting 4,5-difluoro-6-arylpicolinate (the compound of Formula II) to florpyrauxifen-benzyl (Formula I). The method includes the steps of:

a) combining a compound of Formula II and anhydrous ammonia;

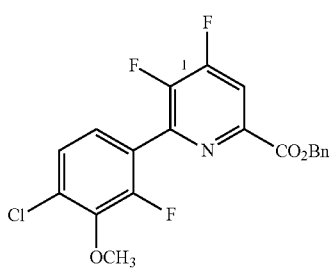

b) isolating a compound of Formula III from the combination of step a);

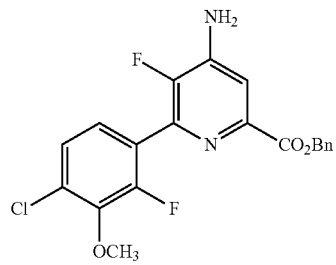

c) combining the isolated compound of Formula III from step b) with anhydrous HCl to form an HCl salt of Formula IV;

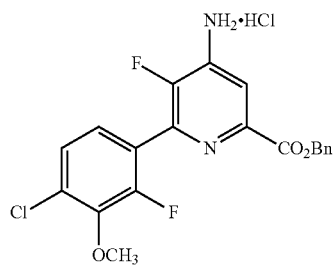

d) isolating the compound of Formula IV from step c) and combining the isolated compound of Formula IV with a base to reform the compound of Formula III;

e) adding a chlorinating agent to the combination of step d); and f) isolating the compound of Formula I.

The method may alternatively include reisolating the compound of Formula III after step d) prior to adding the chlorinating agent in step e).

DETAILED DESCRIPTION

A method for preparing florpyrauxifen-benzyl (Formula I) from a 4,5-difluoro-6-arylpicolinate of Formula II is provided. As illustrated in Scheme 1, the method includes chemical process steps that introduce: (1) the 4-amino group by amination of the compound of Formula II with ammonia and (2) the 3-chloro group by chlorination with an N-chloro compound.

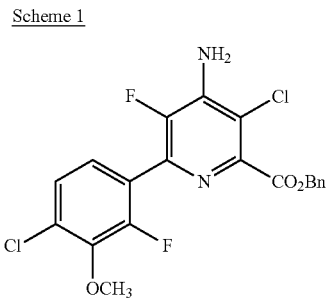

I. Definitions

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. In some embodiments, the heteroaryl group can be a pyridyl, pyrimidyl or a triazinyl group. The aryl or heteroaryl substituents may be unsubstituted or substituted with one or more chemical moieties. Examples of suitable substituents include, for example, amino, halo, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_{10}$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl, $C_1$-$C_{10}$ alkoxycarbonyl and $C_1$-$C_2$ haloalkyl.

As used herein, the term "Bn" as used in a chemical structure drawing (i.e., the compounds of Formula I, II, III, IIIa, IIIb, or IV) refers to a benzyl group, which can also be represented as $PhCH_2$.

As described herein, the compound of Formula III is

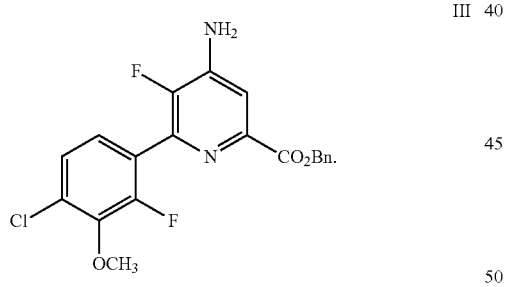

III

The compound of Formula III may be prepared in different ways. For clarity in the description, the compound formed in different ways may be represented as the compound of Formula IIIa or the compound of Formula IIIb, depending on how it is prepared. When the compound of Formula III is prepared by amination of the difluoropicolinate compound of Formula II with ammonia, it is referred to as the compound of Formula IIIa. When the compound of Formula III is prepared by neutralizing the HCl salt of the compound of Formula IV with a base, it is referred to as compound of Formula IIIb.

II. Amination of Difluoropicolinate II

The first step of the method to prepare the compound of Formula I involves the conversion of the difluoropicolinate of Formula II to the hydrochloride (HCl) salt of Formula IV by amination with ammonia and then treatment with anhydrous HCl (Scheme 3).

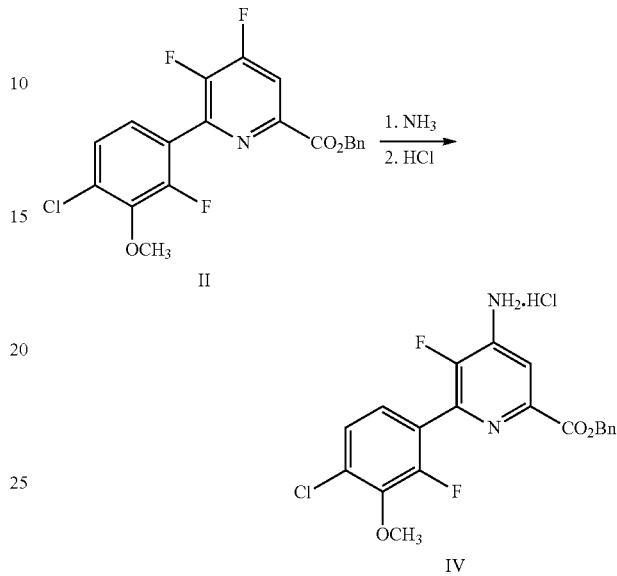

The difluoropicolinate can be first reacted with anhydrous ammonia under pressure to furnish the 4-aminopyridine of Formula IIIa and by-product $NH_4F$ (Scheme 4). After removal of the $NH_4F$ and excess ammonia, the 4-aminopyridine of Formula IIIa was then treated with anhydrous HCl to produce the 4-amino-3-fluoropicolinate HCl salt of Formula IV (Scheme 3). Formation of the HCl salt of Formula IV allows for convenient product isolation.

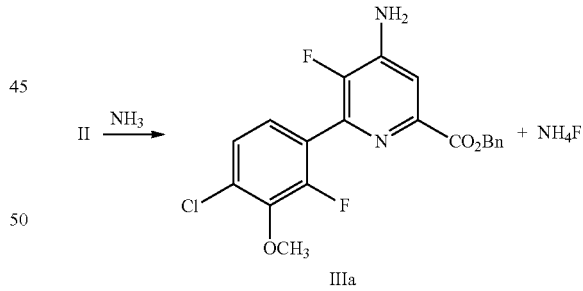

Solvents that may be suitable for use in the amination reaction include, but are not limited to, aprotic solvents such as acetonitrile, propionitrile, benzonitrile, toluene, a xylene, a mixture of xylenes, ethers such as THF, dioxane, mono- and diethyleneglycol ethers, and mono- and dipropyleneglycol ethers, and mixtures thereof.

It has been found that use of acetonitrile ($CH_3CN$) as the reaction solvent for the amination reaction to produce the compound of Formula IIIa offers benefits over other solvents, such as very polar solvents like DMSO and NMP. Even though use of these very polar solvents provides rapid amination of the compound of Formula II at low temperatures, very inefficient aqueous workup procedures are required to isolate the product. In addition, formation and isolation of the HCl salt of Formula IV are not feasible in these very polar solvents. Therefore, use of these very polar solvents does not provide an efficient and scalable amination method to prepare the compound of Formula IIIa or the HCl salt of Formula IV.

Conducting the amination of the difluoropicolinate of Formula II in acetonitrile solvent, under an elevated pressure of anhydrous ammonia and at elevated reaction temperatures provides acceptable reaction cycle times, very good product yields and lower impurity formation. Table 1 shows the results for conducting the amination of the compound of Formula II at various temperatures, pressures and reaction times. As indicated in Table 1, the best conditions for conducting the amination of the compound of Formula II were surprisingly found to be a temperature of about 100° C., an ammonia pressure of about 100 psig and about 2 hours of reaction time to provide the 4-aminopicolinate of Formula IIIa in 85% yield (97% conversion).

TABLE 1

Reaction of Difluoropicolinate II with Ammonia in CH$_3$CN in a 300 mL Parr Reactor.

| Entry | Temperature (° C.) | Pressure[1] (psig) | Time (hours) | Conversion (%) | In Pot Yield (%) IIIa |
|---|---|---|---|---|---|
| 1 | 100 | 40 | 16 | 95 | 84 |
| 2 | 100 | 80 | 7 | 98 | 85 |
| 3 | 100 | 100 | 2 | 97 | 85 |
| 4 | 80 | 100 | 2 | 93 | 80 |
| 5 | 50 | 100 | 3 | 99 | 60 |

[1]The Parr reactor was heated to the indicated temperature and then pressurized with anhydrous ammonia to the indicated pressure.

Surprisingly, decreasing the reaction temperature to 50° C., while maintaining the ammonia pressure at 100 psig (Entry 5), led to a decreased yield of the compound of Formula IIIa even though the conversion was 99%.

The amination reaction to produce the compound of Formula IIIa may be conducted in acetonitrile solvent in a pressure reactor with anhydrous ammonia at a temperature of at least about 60° C., at least about 65° C., at least about 70° C., at least about 75° C., at least about 80° C., at least about 85° C., at least about 90° C., at least about 95° C., at least about 100° C., at least about 105° C., at least about 110° C., or at least about 115° C. Alternatively, the amination reaction to produce the compound of Formula IIIa can be conducted in acetonitrile at a temperature between about 60° C. to about 130° C., or between about 80° C. to about 120° C. In another example, the amination reaction to produce the compound of Formula IIIa can be conducted in acetonitrile at a temperature of between about 90° C. and about 110° C.

The amination reaction to produce the compound of Formula IIIa may be conducted in acetonitrile solvent in a pressure reactor with anhydrous ammonia, wherein the pressure in the reactor is maintained between about 40 to about 150 pounds per square inch gauge (psig), between about 50 to about 140 psig, between about 50 to about 120 psig, between about 50 to about 100 psig, between about 60 to about 130 psig, between about 70 to about 120 psig, between about 80 to about 110 psig, or between about 90 to about 110 psig by adding anhydrous ammonia to the reactor. During the amination reaction the pressure in the reactor may vary somewhat from these pressure ranges due to the periodic addition and consumption of the anhydrous ammonia in the reactor.

Following completion of the amination of the compound of Formula II to produce the compound of Formula IIIa, the pressure reactor was cooled, the pressure vented, the reaction mixture filtered or centrifuged to remove byproduct ammonium fluoride and a filtrate was obtained. The filtrate was then subjected to distillation (i.e., an atmospheric pressure or reduced pressure distillation) to remove substantially all of the residual ammonia and to concentrate the solution containing the crude compound of Formula IIIa to a concentration of no more than about 20 wt %, no more than about 15 wt %, no more than about 10 wt %, or no more than about 5 wt % of the compound of Formula IIIa. The filtrate may also be sparged with a stream of an inert gas such as, for example, nitrogen gas to remove or reduce the amount of residual ammonia.

As used herein, the phrase "remove substantially all of the residual ammonia" is intended to mean removing enough ammonia from the filtrate to reach a final ammonia concentration in the filtrate of less than about 500 ppm. Additionally, the final ammonia concentration can be less than about 250 ppm, less than about 125 ppm, less than about 63 ppm, less than about 32 ppm, or less than about 16 ppm.

The post-amination reaction mixture containing the crude compound of Formula IIIa, after removal of the byproduct NH$_4$F by filtration or centrifugation and substantially all of the residual ammonia by distillation or sparging with nitrogen gas, was treated with anhydrous HCl. The resulting mixture was then filtered or centrifuged to provide the HCl salt of Formula IV. In some examples, between about 1.0 to about 5.0, between about 1.0 to about 2.0, between about 1.0 to about 1.5, or between about 1.0 to about 1.2 molar equivalents of anhydrous HCl, relative to the compound of Formula IIIa, may be used to prepare the HCl salt of Formula IV.

The preparation of the HCl salt of Formula IV may be conducted at a temperature between about 25° C. to about 75° C., between about 25° C. to about 65° C., between about 35° C. to about 65° C., between about 45° C. to about 65° C., between about 45° C. to about 55° C., between about 45° C. to about 75° C., or between about 55° C. to about 75° C. Alternatively, the formation of the HCl salt of Formula IV may be conducted at a temperature between about 40° C. to about 60° C.

The purity of the isolated HCl salt of Formula IV can be at least about 75 weight percent (wt %), at least about 80 wt %, at least about 85 wt %, at least about 87 wt %, at least about 89 wt %, at least about 90 wt %, at least about 91 wt %, at least about 92 wt %, at least about 93 wt %, at least about 94 wt %, or at least about 95 wt %.

Other acids that may be suitable for preparing an acid derived salt of the compound of Formula IIIa include, but are not limited to, HBr, MeSO$_3$H, H$_2$SO$_4$, H$_3$PO$_4$, HNO$_3$, and HBF$_4$.

III. Chlorination of 4-Aminopicolinate IIIb

The next step of the method to prepare the compound of Formula I involves the conversion of the HCl salt of Formula IV to florpyrauxifen-benzyl (Formula I). This conversion is shown in Scheme 5 and involves neutralizing the HCl salt of Formula IV with a base to furnish the 4-aminopicolinate of Formula IIIb and then converting the compound of Formula IIIb into the compound of Formula I by utilizing a chlorinating agent that is an N-chloro compound.

Scheme 5

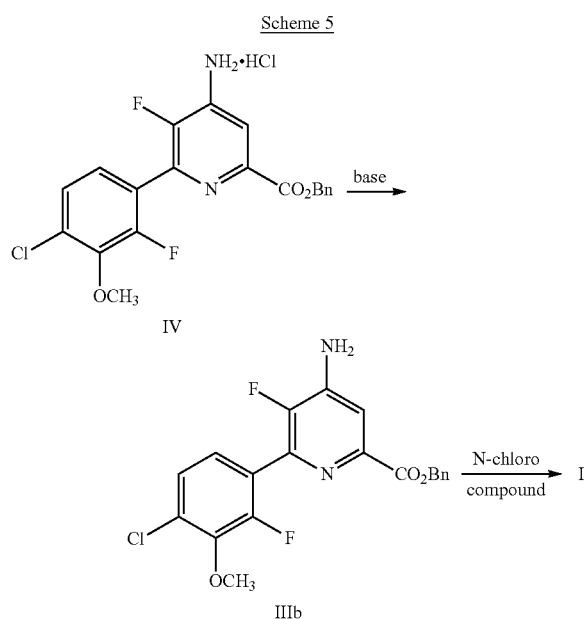

A. Two-Phase Solvent System for Neutralizing IV and Isolating IIIb

A two-phase solvent system may be used for neutralizing the HCl salt of Formula IV with a base and reisolating the 4-aminopicolinate of Formula IIIb. The two-phase solvent system may comprise water (i.e., an aqueous liquid phase) and an organic solvent (i.e., a water immiscible liquid phase) selected from aromatic hydrocarbons such as toluene, a xylene, and a mixture of xylenes, benzonitrile, esters such as ethyl acetate, ethers such as tert-amyl methyl ether (TAME), and methyl tert-butyl ether (MTBE), chlorinated hydrocarbons such as dichloromethane and 1,2-dichloroethane, and mixtures thereof. Suitable bases for neutralizing the HCl salt of Formula IV to produce the 4-aminopicolinate of Formula IIIb when using the two-phase solvent system may include, but are not limited to, trialkylamines such as triethylamine, dialkylamines, monoalkylamines, ammonia, and heterocyclic amines such as pyridine and N-methylimidazole. Additional bases that may be used for neutralizing the HCl salt of Formula IV when using the two-phase solvent system may include inorganic bases such as, but not limited to, NaOH and KOH, and carbonates such as $Na_2CO_3$ and $K_2CO_3$.

The water portion of the two-phase solvent system may be added to the neutralizing reaction either before or after addition of the base. The water serves to easily remove the salt (i.e., $Et_3N.HCl$, NaCl or KCl) produced during the neutralizing reaction by washing it out and thereby allowing for reisolation of the 4-aminopicolinate of Formula IIIb as a solution in the water immiscible solvent.

The two-phase solvent system neutralizing reaction can be conducted at a temperature ranging between about 25° C. to about 100° C., between about 25° C. to about 90° C., between about 35° C. to about 90° C., between about 45° C. to about 90° C., between about 55° C. to about 90° C., between about 60° C. to about 90° C., or between about 70° C. to about 90° C.

Following removal of the aqueous phase from the two-phase neutralizing reaction mixture (reisolation of IIIb), the remaining organic solution containing the 4-aminopicolinate of Formula IIIb can be subjected to distillation to remove any water and/or residual base, and to concentrate the solution.

B. Chlorination of Reisolated IIIb

The concentrated solution containing the 4-aminopicolinate of Formula IIIb prepared as described herein can then be treated with a chlorinating agent to introduce a chlorine group onto the pyridine ring of the 4-aminopicolinate of Formula IIIb to produce the final product of Formula I.

The chlorination reaction to produce the final product of Formula I may be conducted at a temperature ranging between about 25° C. to about 120° C., between about 40° C. to about 120° C., between about 50° C. to about 120° C., between about 60° C. to about 110° C., between about 70° C. to about 110° C., between about 70° C. to about 100° C., between about 70° C. to about 90° C., or between about 75° C. to about 85° C.

The chlorinating agent used to prepare the compound of Formula I from the 4-aminopicolinate of Formula IIIb can be an N-chloro compound. Suitable N-chloro compounds that may be used to prepare I include, but are not limited to, 1,3-dichloro-5,5-dimethylhydantoin (DCDMH), N-chlorosuccinimide, 1,3,5-trichloro-2,4,6-triazinetrione, N-chlorosaccharin, and N-chlorophthalimide. A useful chlorinating agent used to prepare the compound of Formula I is 1,3-dichloro-5,5-dimethylhydantoin.

B. One-Phase Solvent System for Neutralizing IV and Chlorinating IIIb

A one-phase solvent system (i.e., a single organic liquid phase and no liquid aqueous second phase) may be used for the neutralization of the HCl salt of Formula IV with a base to produce the 4-aminopicolinate of Formula IIIb. The one-phase solvent system may comprise an organic solvent such as, but not limited to, aromatic hydrocarbons such as toluene, a xylene, and a mixture of xylenes, acetonitrile, benzonitrile, esters such as ethyl acetate, ethers such as THF, dioxane, tert-amyl methyl ether (TAME), and methyl tert-butyl ether (MTBE), chlorinated hydrocarbons such as dichloromethane and 1,2-dichloroethane, and mixtures thereof. Suitable bases for neutralizing the HCl salt of Formula IV to produce the 4-aminopicolinate of Formula IIIb when using the single-phase solvent system may include, but are not limited to, trialkylamines such as triethylamine, dialkylamines, monoalkylamines, ammonia, and heterocylic amines such as pyridine and N-methylimidazole.

The single-phase solvent system neutralizing reaction can be conducted at a temperature ranging between about 25° C. to about 100° C., between about 25° C. to about 90° C., between about 35° C. to about 90° C., between about 45° C. to about 90° C., between about 55° C. to about 90° C., between about 60° C. to about 90° C., or between about 70° C. to about 90° C.

Following neutralization of the HCl salt of Formula IV with the base to produce the 4-aminopicolinate of Formula IIIb using the single-phase solvent system, the resulting mixture can then be treated with a chlorinating agent to introduce a chlorine group onto the pyridine ring of 4-aminopicolinate IIIb to produce the final product of Formula I. As an example, the chlorinating agent used to prepare the compound of Formula I from the 4-aminopicolinate of Formula IIIb using the single-phase solvent system can be an N-chloro compound. Suitable N-chloro compounds that may be used to prepare I include those described herein.

The chlorination reaction to produce the final product of Formula I using the single-phase solvent system may be conducted at a temperature ranging between about 25° C. to about 120° C., between about 40° C. to about 120° C., between about 50° C. to about 120° C., between about 60° C. to about 110° C., between about 70° C. to about 110° C., between about 70° C. to about 100° C., between about 70° C. to about 90° C., or between about 75° C. to about 85° C.

III. Isolation/Purification

After preparation of the compound of Formula I by the process described herein, the product may be isolated by employing standard isolation and purification techniques. For example, the crude product may be isolated using standard methods as described herein and purified by crystallization using a single solvent or a mixture of two or more solvents. The solvent or solvents used in the crystallization may include one or more of an aliphatic hydrocarbon, an aromatic hydrocarbon and an alcohol.

The crude product of Formula I may be purified by crystallization from a single solvent selected from the group including aromatic hydrocarbons and $C_4$-$C_{12}$ alcohols such as, for example, toluene, a xylene, a mixture of xylenes, 1-butanol, 2-butanol, 2-methyl-1-propanol, 2-methyl-2-propanol, 1-pentanol, 2-pentanol, 2-methyl-2-butanol, 1-hexanol, 2-hexanol, 3-methyl-1-pentanol, cyclohexanol, 1-heptanol, 2-heptanol, 1-octanol, 2-octanol, 2-ethyl-1-hexanol, 2-propyl-1-heptanol, 1-nonanol, 1-decanol, 1-undecanol, and 1-dodecanol. In one embodiment, the crude product of Formula I may be purified by crystallization from 2-ethyl-1-hexanol. In another embodiment, the crude product of Formula I may be purified by solvent exchange (i.e., removal of one solvent and replacement of it with a second solvent) and crystallization from the second solvent. For example, a solution of the crude product of Formula I in toluene may be subjected to distillation to remove the toluene and allow replacement of it with a second solvent that is 2-ethyl-1-hexanol.

The crude product of Formula I may also be purified by recrystallization from a combination of two or more solvents selected from the group including aliphatic hydrocarbons, aromatic hydrocarbons and $C_4$-$C_{12}$ alcohols. For example, the crystallization of the crude product of Formula I may be conducted with a combination of an aliphatic hydrocarbon, such as hexane or a mixture of hexanes, and an aromatic hydrocarbon such as toluene. Additionally, the recrystallization of the crude product of Formula I may be conducted with a combination of an aromatic hydrocarbon and a $C_4$-$C_{12}$ alcohol. Additionally, the recrystallization of the crude product of Formula I may be conducted with a combination of an aliphatic hydrocarbon and a $C_4$-$C_{12}$ alcohol.

The crude product of Formula I may also be purified by dissolving it in one solvent to form a solution and then adding a second solvent to the solution to cause the product of Formula I to crystallize out of the mixture of the two solvents. For example, a solution of the crude product of Formula I in an aromatic hydrocarbon solvent such as toluene may be treated with an aliphatic hydrocarbon solvent such as hexane or a mixture of hexanes to cause crystallization of the product of Formula I from the mixture of the two solvents.

The following examples are presented to illustrate the methods and compositions described herein.

EXAMPLES

Example 1. Preparation of benzyl 4-amino-5-fluoro-6-(4-chloro-2-fluoro-3-methoxyphenyl)picolinate hydrochloride A. A 300 mL Parr reactor was charged with benzyl 4,5-difluoro-6-(4-chloro-2-fluoro-3-methoxyphenyl)picolinate (15 grams, 78.9 wt %, 29.1 mmol) and 125 grams of acetonitrile. The reactor was pressured and then vented with 350 psi nitrogen three times to ensure removal of oxygen. Stirring was initiated and the solution was heated to 100° C. Upon reaching temperature, ammonia was fed to the reactor over 6 minutes, bringing the reactor to a final pressure of 80 psi. The reaction mixture was left to stir for 5 hours, during which time the reactor pressure was maintained at 80 psi by feeding additional ammonia when necessary. Upon completion of the reaction as determined by HPLC, the solution was cooled and vented to remove the excess ammonia. The crude solution was filtered to remove the ammonium fluoride byproduct and the resulting reactor solution was analyzed by HPLC which indicated the in-pot yield of the benzyl 4-amino-5-fluoro-6-(4-chloro-2-fluoro-3-methoxyphenyl) picolinate intermediate was 85% as determined by using a quantitative internal standard method. The solution was briefly heated to 82° C. and distilled at ambient pressure to remove any residual ammonia and to concentrate the solution to approximately 20 wt % solids loading. The solution was then cooled to 50° C. and treated with a solution of 12.3 wt % HCl in acetonitrile (26.4 mmol) by drop-wise addition over 3 mins. The resulting slurry was stirred for 1 hour and then filtered at 50° C. The wet cake was washed with room temperature acetonitrile and dried overnight in a vacuum oven, affording the desired 4-amino-5-fluoro-6-(4-chloro-2-fluoro-3-methoxyphenyl)picolinate hydrochloride as a brown solid (91.7 wt %, 70% yield).

B. A 5-Liter Hastelloy C jacketed reactor was charged with benzyl 4,5-difluoro-6-(4-chloro-2-fluoro-3-methoxyphenyl)picolinate (325 grams, 81.3 wt %, 0.65 mol) and 2395 grams of acetonitrile. The reactor was pressurized to 175 psig with nitrogen and vented three times to ensure removal of oxygen. Stirring was initiated and the solution was heated to 100° C. Upon reaching temperature, ammonia was fed to the reactor over 30 minutes, bringing the reactor to a final pressure of 80 psig. The reaction mixture was left to stir for 4 hours, during which time the reactor pressure was maintained at 80 psig by feeding additional ammonia when necessary. Upon completion of the reaction as determined by HPLC, the solution was cooled and vented to remove the excess ammonia. The crude solution was filtered to remove the ammonium fluoride byproduct and transferred to a 5-liter glass jacketed reactor. The ammonium fluoride wet cake was washed with 415 g of additional acetonitrile. The wash filtrate was combined with the original reactor solution in the 5-liter glass reactor. The combined solution was analyzed by HPLC, which indicated the in-pot yield of the benzyl 4-amino-5-fluoro-6-(4-chloro-2-fluoro-3-methoxyphenyl)picolinate intermediate was 83% as determined by using a quantitative internal standard method. The solution was briefly heated to 60° C. and distilled under vacuum (365 mmHg) to remove any residual ammonia and to concentrate the solution to approximately 14 wt % desired product loading. The solution was then cooled to 50° C. and sparged with HCl (24.8 g, anhydrous, 0.68 mol) over 50 mins. The resulting slurry was stirred for 30 mins and then filtered at 50° C. The wet cake was washed with room temperature acetonitrile (321 g) and dried overnight in a vacuum oven, affording 238 g of the desired 4-amino-5-fluoro-6-(4-chloro-2-fluoro-3-methoxyphenyl)picolinate hydrochloride as a brown solid (93.2 wt %, 77% yield).

Example 2. Preparation of benzyl 4-amino-3-chloro-5-fluoro-6-(4-chloro-2-fluoro-3-methoxyphenyl)picolinate A. A mixture of 200.0 g of 4-amino-5-fluoro-6-(4-chloro-2-fluoro-3-methoxyphenyl)picolinate hydrochloride (93.2 wt %, 0.42 mol) and 1440 g toluene were placed into a 5-Liter jacketed reactor outfitted with a condenser and overhead stirring. The solution was placed under nitrogen atmosphere and treated with triethylamine (44.9 g, 0.44 mol). The mixture was then heated to 80° C. and stirred for an additional 0.5 hr. The resulting solution was washed with 1780 g of water twice. The aqueous washes were discarded and the reactor solution was heated to 80° C. and distilled under vacuum (300 mmHg) to remove any residual water and triethylamine. The solution was then treated with DCDMH (1,3-dichloro-5,5-dimethylhydantoin, 51.0 g, 0.25 mol) and left to stir for 2.5 hours at 75° C. Upon completion of the reaction as determined by HPLC analysis, the cooled solution was then washed with 1290 g of aqueous sodium bisulfite (0.7 wt %, 0.08 mol) and then 1500 g of water. The combined aqueous washes were discarded and the organic solution was then heated to 80° C. and distilled again under vacuum (300 mmHg) to concentrate the solution and remove any residual water. The solution was concentrated to approximately a 17 wt % of the product, cooled to 70° C. and then approximately 790 g of hexanes were added drop-wise to the solution over 90 mins, which was subsequently cooled back to room temperature. The resulting mixture was filtered and the resulting wet cake was washed with a mixture consisting of 300 g of toluene and 300 g of hexanes. The wet cake was then dried overnight in a vacuum oven at 70° C. to afford the desired product in 84% yield as an yellow solid (166 g, 92.2 wt %).

B. A mixture consisting of 200.4 g 4-amino-5-fluoro-6-(4-chloro-2-fluoro-3-methoxyphenyl)picolinate hydrochloride (80.2% purity), 38.9 g TEA and 2038 g toluene was placed in a 4.5 L jacketed reactor. The resulting slurry was placed under nitrogen atmosphere and heated to 80° C. Then solution was then washed with 1511 g of water, followed by a second wash with 1302 g water. The resulting organic layer was vacuum-transferred to a 3.5 L jacketed reactor along with 124 g of a toluene rinse. The solution was then distilled under vacuum to remove the excess water. Upon removal of the water, approximately 43.9 g of 1,3-dichloro-5,5-dimethylhydantoin (0.6 equivalents) was added to the reactor over 12 minutes. The solution was stirred at 75° C. for 4 hours, and an additional 1.35 g of 1,3-dichloro-5,5-dimethylhydantoin (0.02 equivalents) was added to complete the reaction. After 90 min, a mixture consisting of 19 g of 40% (w/w) aqueous sodium bisulfite solution and 1000 g warm tap water was added to the reactor. The reactor was heated to 80° C., and the aqueous layer was decanted. An additional 1000 g warm tap water was added for a second aqueous extraction. As before, the mixture was heated to 80° C. and the aqueous layer was decanted. At this point, the toluene was distilled overhead at 80° C. under vacuum to perform a solvent exchange. Upon removal of the bulk of the toluene, 595 g of 2-ethyl-1-hexanol was poured into the reactor. The distillation was resumed for 80 min until the final pressure in the reactor was 53 mm Hg and the final temperature was 91.6° C. (approximately 60 mL collected overhead). At this point, an additional 563 g 2-ethyl-1-hexanol was poured into the reactor, and the solution was heated to 82° C. and then cooled to 20° C. The resulting slurry was filtered and the collected wet cake solid was washed with 207 g of 2-ethyl-1-hexanol and then with 192 g of hexanes, and partially dried in a vacuum oven. The partially dried wet cake solid was reslurried with hexanes, and finally dried fully in a vacuum oven overnight. The final isolated yield of benzyl 4-amino-3-chloro-6-(4-chloro-2-fluoro-3-methoxyphenyl)-5-fluoropicolinate was 142.0 g (84% yield) at 95.2 wt % purity.

C. A mixture consisting of 4-amino-5-fluoro-6-(4-chloro-2-fluoro-3-methoxyphenyl)picolinate hydrochloride (50.0 g, 88.6 wt %, 100.3 mmol) and 253 g toluene was charged to a 1 L jacketed reactor. The resulting slurry was placed under nitrogen atmosphere and heated to 83° C. The solution was then treated with a 50 wt % solution of triethylamine in toluene (23.3 g, 115.5 mmol). The solution was then cooled to 40° C. and subsequently treated with 1,3-dichloro-5,5-dimethylhydantoin (13.5 g, 67.8 mmol). The solution was reheated to 80° C. over 1 hour and then washed with 248 g of water twice. At this point, the toluene was distilled overhead at 80° C. under vacuum to perform the solvent exchange. Upon removing the bulk of the toluene, 148 g of 2-ethyl-1-hexanol was poured into the reactor. The distillation was resumed to remove the remainder of the toluene until the final pressure in the reactor was 75 mm Hg and the final temperature was 87° C. Next, an additional 153 g of 2-ethyl-1-hexanol was poured into the reactor, and the solution was slowly cooled to 6° C. The slurry was filtered and the resulting wet cake was washed with 145 g heptanes. The washed wet cake was dried in a vacuum oven overnight affording 39.9 g of the desired benzyl 4-amino-3-chloro-6-(4-chloro-2-fluoro-3-methoxyphenyl)-5-fluoropicolinate product (84% yield) with 92.9 wt % purity.

D. Purification: A 74.18 g sample of a solution containing 13.0 wt % benzyl 4-amino-3-chloro-6-(4-chloro-2-fluoro-3-methoxyphenyl)-5-fluoropicolinate in toluene was added to a 250 mL jacketed reactor along with an additional 14.5 g toluene. The slurry was heated to 80° C. and distilled under vacuum to remove a portion of the toluene. When the liquid level in the reactor was sufficiently low, 18.1 g 2-ethyl-1-hexanol (2EH) was added to the reactor, and the solution was further distilled to remove more toluene. When the distillation conditions reached 84 mm Hg vacuum and 88° C., the distillation was stopped, 17.2 g 2EH was added to the reactor, and the solution was sampled by both LC and GC to determine the benzyl 4-amino-3-chloro-6-(4-chloro-2-fluoro-3-methoxyphenyl)-5-fluoropicolinate assay and solvent composition. Based on these results, 26.69 g 2EH, 17.58 g heptanes, and 4.47 g toluene were added to the reactor. The mixture was heated to 81° C., then cooled to 20° C. over 6 hours. The resultant slurry was filtered and washed with 40 g hexanes to produce 16.33 g benzyl 4-amino-3-chloro-6-(4-chloro-2-fluoro-3-methoxyphenyl)-5-fluoropicolinate wet cake. This solid was dried in a vacuum oven overnight to afford 9.08 g benzyl 4-amino-3-chloro-6-(4-chloro-2-fluoro-3-methoxyphenyl)-5-fluoropicolinate (87% yield) at 93.8 wt % purity.

The compositions and methods of the claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

What is claimed is:

1. A method for preparing the compound of Formula I:

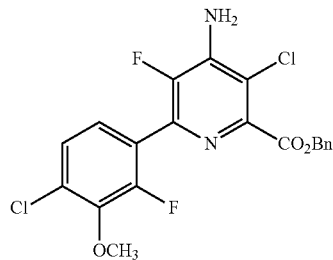

comprising the steps of:
a) combining a compound of Formula II, anhydrous ammonia, and a solvent selected from acetonitrile, propionitrile, benzonitrile, toluene, xylene, THF, dioxane, mono- and diethyleneglycol ethers, mono- and dipropyleneglycol ethers, tert-amyl methyl ether (TAME), methyl tert-butyl ether (MTBE1), or a mixture thereof; and maintaining a pressure of from about 40 to about 150 pounds per square inch gauge (psig) with anhydrous ammonia;

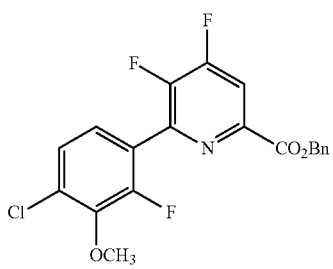

b) isolating a compound of Formula III from the combination of step a);

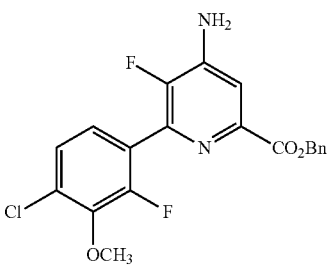

c) combining the isolated compound of Formula III from step b) with anhydrous HCl to form an HCl salt of Formula IV;

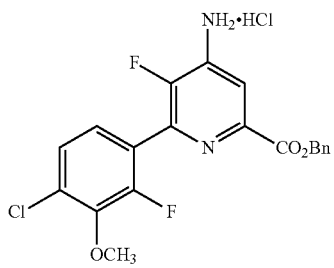

d) isolating the compound of Formula IV from step c) and combining the isolated compound of Formula IV with a base to reform the compound of Formula III;
e) adding a chlorinating agent to the combination of step d); and
f) isolating the compound of Formula I.

2. The method of claim 1, further comprising reisolating the compound of Formula III after step d) prior to adding the chlorinating agent in step e).

3. The method of claim 1, wherein the solvent is acetonitrile.

4. The method of any of claim 1, wherein the combination of step a) is maintained at a pressure of from about 70 to about 100 pounds per square inch gauge (psig) with anhydrous ammonia.

5. The method of claim 1, wherein the combination of step a) is maintained at a temperature of from about 60 to about 130° C.

6. The method of any of claim 1, wherein the combination of step a) is maintained at a temperature of from about 80 to about 120° C.

7. The method of claim 1, wherein step b) comprises removing ammonium fluoride and substantially all of the residual ammonia from the combination of step a).

8. The method of claim 7, wherein the ammonium fluoride is removed by filtration or centrifugation.

9. The method of claim 7, wherein the residual ammonia is removed by distillation or by sparging with an inert gas.

10. The method of claim 1, wherein isolating the compound of Formula IV in step d) comprises isolating the compound of Formula IV by filtration or centrifugation.

11. The method of claim 2, wherein reisolating the compound of Formula III further comprises an aromatic hydrocarbon solvent, toluene, xylene, or benzonitrile.

12. The method of claim 1, wherein the base in step d) comprises triethylamine.

13. The method of claim 2, wherein reisolating the compound of Formula III comprises washing with water.

14. The method of claim 1, wherein the chlorinating agent in step e) is 1,3-dichloro-5,5-dimethylhydantoin.

15. The method of claim 1, wherein the combination in step d) comprises a one-phase solvent system comprising a solvent selected from toluene, xylene, acetonitrile, benzonitrile, ethyl acetate, THF, dioxane, tert-amyl methyl ether (TAME), methyl tert-butyl ether (MTBE) and/or a chlorinated hydrocarbon selected from dichloromethane and 1,2-dichloroethane.

16. The method of claim 1, wherein after isolation in step f) the compound of Formula I is purified by crystallization from a solvent comprising 2 ethyl-1-hexanol.

17. The method of claim 1, wherein after isolation in step f) the compound of Formula I is purified by crystallization from a solvent mixture comprising an aliphatic hydrocarbon that is a hexane or a mixture of hexanes, and an aromatic hydrocarbon that is toluene.

18. The method of claim 1, wherein after isolation in step f) the compound of Formula I is purified by crystallization from a solvent mixture comprising 2-ethyl-1-hexanol, heptanes, and toluene.

* * * * *